United States Patent
Hance et al.

(10) Patent No.: US 7,789,039 B2
(45) Date of Patent: Sep. 7, 2010

(54) HYDROGEL BEADS OR CAPSULES AS ARTIFICIAL MEDIA FOR INSECTS OVIPOSITION AND REARING OF ENDOPARASITOIDS

(75) Inventors: Thierry Hance, Autre-Eglise (BE); Michèle Debatty-Mestdagh, Brussels (BE); Vincent Cambier, Louvain-la-Neuve (BE); Catherine Boegen, Andenne (BE); Frédéric Muratori, Liège (BE); Olivier Lebbe, Spy (BE); Ana-Maria Dos Santos Goncalves, Brussels (BE)

(73) Assignee: Université Catholique de Louvain, Louvain-la-Neuve (BE)

( * ) Notice: Subject to any disclaimer, the term of this patent is extended or adjusted under 35 U.S.C. 154(b) by 998 days.

(21) Appl. No.: 10/481,102

(22) PCT Filed: Jun. 21, 2002

(86) PCT No.: PCT/EP02/06936

§ 371 (c)(1),
(2), (4) Date: Jul. 12, 2004

(87) PCT Pub. No.: WO03/000047

PCT Pub. Date: Jan. 3, 2003

(65) Prior Publication Data

US 2004/0231601 A1 Nov. 25, 2004

(30) Foreign Application Priority Data

Jun. 22, 2001 (EP) .................................. 01870134

(51) Int. Cl.
*A01K 67/033* (2006.01)
(52) U.S. Cl. ....................... 119/6.5; 119/6.6
(58) Field of Classification Search ................. 119/6.5, 119/6.6; 43/132.1
See application file for complete search history.

(56) References Cited

U.S. PATENT DOCUMENTS

| 3,893,420 | A | * | 7/1975 | Andreev et al. | 119/6.6 |
|---|---|---|---|---|---|
| 4,418,647 | A | * | 12/1983 | Hoffman | 119/6.6 |
| 4,646,683 | A | * | 3/1987 | Maedgen, Jr. | 119/6.5 |
| 4,701,326 | A | * | 10/1987 | Nelsen et al. | 424/408 |
| 4,753,799 | A | * | 6/1988 | Nelsen et al. | 424/408 |
| 5,127,186 | A | * | 7/1992 | Kreitzer | 47/57.6 |
| 5,170,744 | A | * | 12/1992 | Pruitt et al. | 119/67 |

(Continued)

FOREIGN PATENT DOCUMENTS

EP 0 210 447 A1 2/1987

OTHER PUBLICATIONS

Internet Document, Wayback Machine—http://www.archive.org, Cereal Leaf Beetle: Control Using Parasitic Wasps, initially archived May 2, 1998—see header, wherein the first 8 numerals indicate such "19980502", and of which the most recent page published on the internet is included, the State of North Carolina, 4 pages altogether.*

(Continued)

*Primary Examiner*—Bret Hayes
(74) *Attorney, Agent, or Firm*—Knobbe, Martens, Olson & Bear, LLP

(57) ABSTRACT

Methods and hosts for rearing insect parasitoids are provided. Particularly, polymer beads (alginate, carrageenan, and chitosan) are used to rear endoparasitoids in vitro.

20 Claims, 2 Drawing Sheets

U.S. PATENT DOCUMENTS

| | | | | |
|---|---|---|---|---|
| 5,639,275 | A | * | 6/1997 | Baetge et al. ............ 604/891.1 |
| 5,739,005 | A | * | 4/1998 | Rodriguez-Kabana et al. ......................... 435/40.5 |
| 5,750,126 | A | * | 5/1998 | Smith et al. ................. 424/405 |
| 5,799,607 | A | * | 9/1998 | Greany et al. ................ 119/6.5 |
| 5,899,168 | A | * | 5/1999 | Rojas et al. .................. 119/6.5 |
| 6,004,571 | A | * | 12/1999 | Thies ......................... 424/410 |

OTHER PUBLICATIONS

Battaglia, et al. "Physical and Chemical Cues Influencing the Oviposition Behaviour of *Aphidius ervi;*" *Entomologia Experimentalis et Applicata*, vol. 94. No. 3, pp. 219-227, Mar. 2000.

Digilio, "In vitro rearing of the Aphid Parasitoid *Aphidius ervi* Haliday (Hymenoptera Braconidae)," *Bollettino del Laboratorio di Entomologia Agraria Filippo Silversti*, No. 55, pp. 151-161, 1988.

Grenier, et al., "Potential for Mass Release of Insect Parasitoids and Predators Through Development of Artificial Culture Techniques," *Pest. Management in the Subtropics: Biological Control-a Florida Perspective*, pp. 181-205, 1994.

House, "An Artificial Host: Encapsulated Synthetic Medium for In Vitro Oviposition and Rearing the Endoparasitoid *Itoplectis Conquisitor* (Hymenoptera: Ichneumonidae)," *Canadian Entomologist*, vol. 110, No. 3, pp. 331-334, 1978.

Mogul, et al., "Controlled Release of Biologically Active Agents for Purposes of Agricultural Crop Management," *Resources Conservation and Recycling*, vol. 16, No. 1-4, pp. 289-320, 1996.

International Search Report issued Apr. 14. 2003, to a related, foreign application.

"Cereal Leaf Beetle Control Using Parasitic Wasps," from the North Carolina Department of Agriculture & Consumer Services website (www.ncagr.com) dated Jun. 11, 2002 and printed Jan. 2, 2007, 2 pages.

\* cited by examiner

HYDROGEL BEADS OR CAPSULES AS ARTIFICIAL MEDIA FOR INSECTS OVIPOSITION AND REARING OF ENDOPARASITOIDS

This is the U.S. National Phase under 35 U.S.C. §371 of International Application PCT/EP02/06936, filed Jun. 21, 2002, which claims priority of EP 01870134.2, filed Jun. 22, 2001 Each of the above applications are incorporated herein by reference in their entirety.

FIELD OF THE INVENTION

The present invention relates to the field of insect pest control using biocontrol agents. The invention relates to the use of polymer beads (alginate, carrageenan, chitosan) or capsules to rear endoparasitoids of insects in vitro.

BACKGROUND TO THE INVENTION

The principal method of controlling pests, such as *aphids*, throughout the world is that of treating the infested crop with insecticides. However, there are drawbacks to this method such as environmental pollution, harmfulness for humans and animals, increased resistance in key pests, creation of secondary pest outbreaks, effective elimination of beneficial insects and so forth. Nowadays, there is an increasing interest in reducing the use of pesticides.

An alternative to chemical pesticides is the use of biocontrol agents such as predaceous and parasitoids for controlling insect pests. Nevertheless, millions of these beneficial insects, so-called biocontrol agents, are required for using this method in the fields. At the present time, for the mass production, it is still necessary to rear these insects on their natural hosts, for instance cereal *aphids*. This classical method is too expensive to allow large-scale use of beneficial insects in commercial agriculture. A solution seems to be the development of artificial media to rear these beneficial insects. Indeed, this method will allow reducing the cost of the mass production.

Since many years, the researchers develop methods to raise the beneficial insects (predators and parasitoids) on artificial media. Simmonds (1966) attempted to culture three ectoparasitic ichneumonids of coding moth pupae on nutritive gelatine slants and raw beef. Yazgan (1972) and House (1978) used a dietetic approach to prepare media utilizing existing knowledge of the nutritional requirements of insects generally, to successfully rear the parasitic hymenopteran *Itoplectis conquisitor* (Say) in chemically defined, synthetic diet. House (1978) encapsulated a synthetic diet within a Parafilm RTM capsule and created an artificial host that also served adequately for oviposition and rearing for *I. conquisitor*. Hoffman and Ignoffo (1974) and Hoffman et al., (1975) developed media that allowed at least partial success in rearing the pupal endoparasitoid, *Pteromalus puparum* (L.) and the egg parasitoid *Trichogramma pretiosum* (Riley), respectively.

Grenier et al. (1994) presented a review of over a half century of research on development of artificial media for entomophages, and report successes in producing media for ectoparasitoids and predators but not for endoparasitoids. Curiously, none of these artificial media has found its way into use in the commercial production of any entomophage, and none of these media have been incorporated into the augmentative production systems for these predators.

In order to fight against *aphids*, the most important pest insects in the agriculture of the temperate climatic zones, endoparasitoids are often effective biological control agents. Nevertheless, the number of parasitoids in the crops are often too low to reduce strongly the aphid populations. Thus, inundate releases of these beneficial insects are essential. Unfortunately, at the present time no artificial medium to rear these endoparasitoids was developed.

Despite considerable effort, no hymenopterous larval endoparasitoid has been successfully reared from egg to adult in artificial media. However, partial success has been attained with two braconid larval endoparasitoids, *Microplitis croceipes*. (Cresson) and *Cardiochiles nigriceps* (Viereck), and one braconid larval-pupal endoparasitoid, *Diachasmimorpha longicaudata* (Ashmead). Pennachio et al. (1992) have cultured the *Heliothis virescens* braconid larval endoparasitoid *Cardiochiles nigriceps* from post-germband eggs to the second instar in an artificial medium comprised of an amino acid, salt, vitamin, and carbohydrate-containing medium supplemented with bovine serum albumin, enzymatically hydrolysed lactalbumin, fetal bovine serum, egg yolk and milk. However, the larvae grew much slower than in vivo, only 10% moulted to the second instar and they did not complete development.

It is an aim of the present invention to provide methods and artificial hosts for continuous rearing endoparasitoids.

It is also an aim of the present invention to provide artificial hosts for oviposition of endoparasitoids.

It is a further aim of the invention to provide methods for producing artificial hosts for endoparasitoids.

It is also an aim of the invention to provide a means for storage of artificial hosts containing endoparasitoids and to apply them easily where they are needed for biological control programs.

SUMMARY OF THE INVENTION

Until the present invention, eggs and larvae of hymenopterous endoparasitoid were collected from previously parasitized hosts, sterilised and were immersed in the nutritive solution in vitro. Nevertheless, these handlings could wound the parasitoids, are very time consuming and do not allow actual mass rearing. The invention now provides new hosts for endoparasitoids.

The use of biopolymer beads or capsules as host or recipient for oviposition makes its possible to avoid all handling, for instance by continuously furnish the necessary nutrients by bringing the beads or capsules (after oviposition) into a nutritive and oxygenated solution which allows diffusion through the polymer matrix without removing the media inside the beads. Beads or capsules containing the nutritive solution may be produced in large quantity at low cost and stored for a long time in sterile conditions without loosing their properties before to be used for endoparasitoid production.

The use of biopolymer beads or capsules as hosts or recipient for oviposition makes it possible to avoid all these handlings.

Polymer beads such as alginate and chitosan are used in a variety of areas of biotechnology in encapsulation processes. These beads are used to encapsulate various materials such as enzymes, hormones; drugs, adsorbents and so forth. The viable biomaterials to be encapsulated can also be tissue, organelle, plant or animal cells, bacteria, algae, fungi and so forth. The material must be of a size small enough to be suitable for encapsulation by the droplet method of this invention but can vary widely in diameter from less than a micron to several millimetres.

It is embodied in the present invention to use these polymer beads or capsules to rear endoparasitoids of insects. These beads or capsules would contain a nutritive solution for these endoparasitoids and be coated by substances enhancing oviposition such as epicuticular host (aphid) or other host's compounds and/or of plant extracts. The parasitoid would lay an egg in the beads or capsules with its ovipositor and the larva fed by the nutritive solution would develop in the bead. The beads or capsules may be brought into a continuous flow of sterilized and oxygenated nutritive solution. Indeed as parasitoid larvae in development will consume the nutrient and oxygen present in the nutritive solution, it may be necessary to provide continuously new nutrients. This is possible because of the use of hydrophilic biopolymers which are a matrix containing pores allowing the diffusion of big molecules such as BSA (69 kDa). At the end of the development of the third stage larvae, beads or capsules will be removed, preferably automatically, from the nutritive media and placed in a constant temperature chamber with a relative humidity ranging from 75% to saturation. The larva would then spin a cocoon and after some days, adults would emerge from the beads or capsules. The methods provided by the present invention may reduce considerably the time needed for in vitro rearing as it reduces the hand manipulating needs to nearly nothings, avoiding the risk of damaging the endoparasitoid during its development and allowing industrial automated mass rearing. Concerning the mass release in agricultural field or in every place or time needed for biological control of insect pest by endoparasitoid, the said system will even allow for instance the spraying of a large amount of embedded mummies placed in an adequate solution such as a salt physiological solution (NaCl, 0.07% buffered at a pH ranging from 6 to 7.5) and spraying using a classical pulverisator as currently used by farmers. So, it may represent an ideal system for mass biological control program from the endoparasitoid production to their mass released where needed.

The nutritive medium in order to rear endoparasitoids is a nutritive solution comprising sucrose, amino acids, vitamins, mineral salts and sterols encapsulated in a spherical biopolymer bead or capsule. Preferably, said liquid nutritive solution comprises at least one of the following essential compounds: Trehalose (concentration may range from at least 10 mg to 1 g/100 ml), cholesterol (ranging from at least 10 to 100 mg/100 ml) or other sterols, FBS (fetal bovine serum, at least 1 to 20% v/v) and vitamin C. The pH of the media may range between 6 and 7.5. The polymer used may be an alginate, a carrageenan or a chitosan (and mix of two polymers). Other hydrophilic biopolymers could also be used.

The medium may be encapsulated during the preparation of the beads or capsules and/or may be introduced by diffusion by immersing the beads or capsules in the nutritive solution after their manufacture.

The same nutritive solution may also be used to bring in the beads and the capsules. This medium may be oxygenated and sterilized. For instance, the beads or capsules are placed in a device looking like a fermentor, alimented by a flow of oxygenated and sterilized medium.

DETAILED DESCRIPTION OF THE INVENTION

According to a first embodiment the present invention relates to the use of a polymer or hydrogel bead or capsule as a host for an endoparasitoid.

The term "polymer" or "hydrogel" as herein used are interchangeable and merely relate to the method of manufacture in that a hydrogel is a gel prepared in an aqueous solvent whereas a polymer is a large molecule which is generally built from smaller units or monomers. Preferred are biopolymer beads or capsules.

The term □endoparasitoid□ relates to an insect and especially a wasp that completes its larval development within the body of another insect eventually killing it and is free-living as an adult.

According to a further embodiment, the invention relates to the use of polymer beads or capsules for in vitro rearing of endoparasitoids wherein said beads or capsules are used for oviposition.

The term "oviposition" relates to the laying of eggs by means of an ovipositor, for instance by insects. The term "ovipositor" relates to an organ or set of organs at the end of the abdomen, by which eggs are deposited. According to the present invention, the endoparasitoid will deposit one or several eggs in the polymer bead or capsule.

The term "capsule" relates to a hollow bead composed from a combination of components, further characterised in that during the manufacture of said capsules, a thickener, preferably dextran or lambda carrageenan has been added to the salt solution.

The polymer beads or capsules may be composed of alginate, carrageenan or chitosan. These biopolymers are also chosen because they are natural, non-toxic products which are completely biodegradable and safe for the environment.

Several examples of polymer beads or capsules, composed of one of said components or composed of mixtures of at least two of said components are described in the examples sections.

In the prior art, several methods have been described to prepare polymer beads or capsules. However, in the present invention are described methods for the preparation of polymer beads or capsules which are especially suited for use in methods for rearing insect parasitoids. The preparation of beads or capsules is a modification from protocols described in the literature (Wrong and Somesh, 1995; Velings, 1997; Somesh et al., 1988). The basic protocol used for the preparation of the biopolymer capsules is described in Somesh et al.

However, the capsules prepared using these conditions, did not always result in the deposition of eggs and also the shape of the capsule was highly variable. For instance, when capsules are used, in order to allow oviposition, the thickness of the wall would preferably range between 5 and 100 µm. This is one reason why the literature protocols for preparing capsules had to be modified to produce biopolymers suitable for use in the embodiments of the present invention.

According to another embodiment the invention thus also relates to a method for preparing hydrophilic and porous biopolymer capsules for in vitro rearing of endoparasitoids comprising:

stirring a polymer solution containing between about 0.75 and 1% (w/v) chitosan, and extruding through a needle an ionic solution containing between 1.5 and 3.5% (w/v) pentasodium trippolyphospate and between 10 and 40%, preferably between 10 and 30%, between 15 and 25%, most preferably about 20% Dextran, hereby generating small droplets falling in the polymer solution, preferably the ionic solution is delivered at a rate of 7 ml/min (or about 10 droplets/min), removing the capsules from the polymer solution after a maximum of 5 minutes or alternative after a period of time needed to obtain capsules with a wall thickness between 10 and 100 microns, treating the capsules in pentasodium tripolyphosphate for less than 30 minutes, for instance 25, 20, 15, 10 or 5 minutes, for instance for a period of a maximum of 15 minutes.

Preferably, the diameter of the needle used in these methods is between 0.35 and 0.55 mm, more preferably, the diameter of the needle is 0.45 mm.

With respect of the preparation of the capsules, the modifications concern the concentration of chitosan, the concentration of the ionic solution and the duration of the stay in the chitosan solution which are necessary to provide the beads with the required characteristics and properties.

The duration time in the chitosan (polymer) solution is needed to ensure the formation of the required size of beads or capsule, a correct sphericity and a good repeatability of the beads or capsule formation. For the chitosan capsules, the time the beads are kept in the polymer solution also determines the thickness of the wall of the capsule. If the wall of the capsules is too thick (more than 100 micron), the endoparasitoid is not able to pierce it to lay an egg, as the size of its ovipositor is approximately 100 microns. If the wall of the capsule it is not thick enough, then the capsule will collapse during manipulation. Preferably the size must be between 5 to 10 and 100 microns, most preferably the wall is between 20 and 40 μm, 10 and 50 μm, between 10 and 60 μm, between 10 and 80 μm, or between 30 and 70, or the wall thickness is 25 μm or 35 μm.

The concentration of polyphosphate anions will determine the number of interactions (and their strength) between the chains of polymer (Chitosan) and thus the thickness of the wall. The wall thickness may be measured using an optical microscope or an electronic microscope. The optical microscope is recorded through a camera to a computer, which in function of the magnification used calculates the real thickness. Also other techniques can be used for measuring wall thickness which are well known by the skilled in the art, for instance NMR spectroscopy.

Further, if the maturation time (the time the beads or capsules are treated with pentasodium tri-polyphosphate, is too long (for instance 30 minutes or longer) several layers are observed in the wall of the capsule, and the thickness of the wall being not homogenous for the whole of the capsule area.

Further, agitation of the solutions (e.g. the polymer solution wherein the ionic solution is dropped for preparing the capsules or the pentasodium tri-polyphosphate solution wherein the polymer solution is dropped in case of preparing beads) is needed to ensure a homogenous shape of the capsule, An optimized % of chitosan (preferably between 1 and 0.5%, more preferably 0.75%), % of pentasodium tri-polyphosphate (preferably between 1.5 and 3.5%, more preferably 2.5 or 3%), and optimised pH (pH of the polymer solution obligatory lower than 5.5, preferably 3.5, the pH of the ionic solution may be between 6 and 9, and preferably 7 or 8) are needed to obtain stable capsules with a good sphericity and elasticity to allow the introduction of the ovipositor. If the capsule is too resistant, the parasitoid is not able to lay an egg inside. These conditions are also the better ones to allow a correct porosity and diffusion of the nutrient inside the capsule.

A yellow pigment is added to the capsule, it may be STABILOBOSS™ yellow or any other yellow organic pigment such as lutein. Preferably the beads or capsules are colored by diffusing by adding said pigment at low concentrations, for instance between 1 and 10%, preferably 4 or 5%. An example of the increase in attractivity of yellow pigment is given in Table 1. As such, the invention also relates to biopolymer beads or capsules obtainable by any of the methods described herein and which methods provide the beads or capsules with essential properties for use in rearing endoparasitoids.

As such, the invention also relates to polymer beads or capsules obtainable by any of the methods described herein because these beads or capsules have now the required features that make them suitable for the use of the present invention.

Furthermore, the polymer beads or capsules prepared by any of these methods can be filled with a nutritive solution whereon the larvae can feed when developing from the egg.

Therefore, the present invention more particularly relates to polymer beads or capsules comprising an outer wall composed of a polymer, preferably a biopolymer and more preferable made from alginate, carrageenan, chitosan or a mixture thereof. Said outer wall may consist of one or more layers. The outer wall of the bead or the capsule must have a thickness which is sufficient but not too large to enable the endoparasitoid to enter its ovipositor in it. Further the bead or capsule needs to be hydrophilic and to have a porosity, which allows the entrance of a nutritive solution by diffusion.

Another important feature of the polymer beads or capsules to be suitable for the uses herein described is the diameter of the bead or capsule. Preferably the diameter of the beads or capsules is of approximately the same size as their host. Preferable the diameter of the beads or capsules ranges between 1 and 5 mm, more preferably between 1.5 and 3 mm.

The size of the bead is influenced by the method of preparation. The diameter of the needle determines the size of the drops that fall in the solution and thus determines the size of the capsules or beads. The size is chosen to obtain the best value allowing the manipulation of the beads or capsules by the endoparasitoid prior or during oviposition (antennae contact, walk on the beads or capsules, insertion of the ovipositor). The horizontal position (see FIG. 1) is necessary to obtain spherical capsules or beads and a homogenous distribution of the size and diameter among the capsules or beads produced.

Further, the drop rate must be as high as possible to reduce the duration of time between the moment at which the first drop touches the liquid surface (polymer or ionic solution) and the moment at which the last one enters in contact with the liquid. This is important to avoid a too important difference of stay time in the solution. However the drop rate cannot be too high to avoid obtaining a continuous flow instead of drops.

The viscosity of the drop must be sufficiently high to conserve a spherical shape during the fall and at the moment when the drop enters the solution. If viscosity is too low, than the drop crashes on the liquid surface and flatten or disaggregates in the solution. If viscosity is too high, the liquid moves with difficulty in the tubes and needle of the device. The viscosity is determined by the dextran concentration (Molecular Weight MW). The viscosity thus determines the dextran concentration used.

Preferably, inside the bead or capsule, a cavity is present wherein an egg can be deposited, preferably by an endoparasitoid. It should be clear that eggs or larvae can also be deposited inside these beads, for instance by micro-injection.

Preferably, the said inner cavity is filled with a nutritive solution that allows the hatching of the eggs and the development of the larvae. Said polymer beads or capsules are extremely suited for use as host for endoparasitoids as they allow the passage of oxygen and carbonic gas but also of large range of molecules including Bovine serum albumin (69.000 daltons) because of their hydrophilic nature and the porous matrix they constituted by polymerisation. As the endoparasitoid larva consumes nutrients during its development, beads or capsules may be immersed in the nutritive solution, constantly oxygenated and sterilized using a flow system and a fermentor-like device. Nutrients and oxygen may then diffuse through the beads or capsules' walls to aliment the larva, without any manipulation of the said larva or removal or change of the initial nutritive solution in the bead or capsule.

When preparing the capsules or beads, there are several possibilities to introduce the nutritive media inside. A first option is to immerse the capsules or beads after preparation in the nutritive solution and let nutrients enter by diffusion. The second option is during preparation, for instance of the capsules, to mix the nutritive solution with the dextran and the tripolyphospahte (ionic solution). Then a droplet of that liquid is dropped in the chitosan solution that polymerizes at the surface of the droplet to produce a capsule. The tri-polyphosphate provokes the polymerization, the dextran is used to thicken the solution. In that condition, the solution is trapped inside the capsule during polymerization. In the Examples section such an encapsulation procedure is described.

Preferred nutritive solution contain sucrose, trehalose, aminoacids, vitamins, mineral salts and sterols in defined conditions. Essential compounds that have to be present are: Trehalose (concentration ranging from at least 10 mg to 1 g/100 ml), cholesterol (ranging from at least 10 to 100 mg/100 ml) or other sterols, FBS (fetal bovine serum, from 1 to 20% v/v), vitamin C and choline. Mineral salts are $Na_2HPO_4$, $MgSO_4$ and $CACL_2$. The pH of the media may range between 6 and 7.5. One example of such a nutrient solution, for instance to rear *Aphidius rhopalosiphi* larvae is described in Table 4.

In order to enhance oviposition, beads or capsules may be coated by epicuticular host extracts (such as squalen or octadecyle hexadodecanoate or other alcane, alcene, ester and aldehyde compounds, Table 6 shows some examples), host pheromones such as B-farnesne and/or plant extract. Trehalose has to be present inside the beads or capsules (in concentrations ranging from at least 10 mg to 1 g/100 ml) to increase oviposition. Moreover, capsules or beads are colored in yellow preferably using Stabilo marker ® as yellow colorant. These colored beads or capsules are more stimulating for endoparasitoid and are preferably attacked with regards to their normal host (see FIG. 2, where it can be seen that the (yellow) bead is preferred to real aphid, *Sitobion avenae*) by the endoparasitoid *Aphidius rhopalosiphi*).

In the present invention it is demonstrated that a combination of the biopolymer capsules or beads as described and as prepared by the modified methods, and the yellow colour induce a true oviposition response including the egg laying, and not just an oviposition attack that which does not mean that an egg is really deposited. Indeed, endoparasitoid possess on their ovipositor, nervous sensillae allowing them to probe and to evaluate the host before laying eggs.

The invention thus relates to the use of a polymer bead or capsule as described above as a host for endoparasitoids. In a related embodiment the invention relates to the use of said polymer or hydrogel beads for in vitro rearing of endoparasitoids.

According to a further embodiment the invention relates to the use of polymer beads or capsules for continuous or step by step in vitro rearing of endoparasitoids.

According to a more specific embodiment the invention relates to the use of said biopolymer bead or capsule is used for oviposition and continuous rearing of an endoparasitoid from the egg through to the adult emergence of said endoparasitoid The expression "continuous rearing" or "continuous in vitro rearing" as used herein is marked by a sequence of the developmental stages involving the development of an endoparasitoid from the egg stage to the stage of embedded mummy or adult emergence, without any external manipulation. This is possible by the use of the beads or capsules of the invention which allow all these stages to proceed within the bead or capsule itself, without any manual handling or manipulation of the beads or capsules. Optionally one external manipulation, which is also part of the present invention, is performed i.e. the storage of embedded mummies at low temperatures and high humidity for a further application.

The expression "step by step rearing" as used herein relates to the method of rearing endoparasitoids in a discontinuous way, essentially rearing the endoparasitoids according to the same methods of the continuous way but leaving the possibility of collecting the endoparasitoids at any stage (step) of development and keeping them in a quiescent stage for a defined period of time before re-entering them in the further developmental stage. Since the beads or capsules are nearly transparent, it can easily be monitored in which developmental stage is the endoparasitoid in the bead.

Other moments or stages in the development of the endoparasitoid wherein the development of the endoparasitoid can be rested are for instance the larval stages 1, i.e. just after the egg hatching, 4 to 5 days after oviposition. At that stage, larvae 1, development can be interrupted for several days (2 to 5) by placing them at 5° C. in a nutritive solution.

The Embedded Mummy

According to yet another related embodiment the invention relates to the use of said beads for oviposition, preferably for oviposition of hymenopterous endoparasitoids or insects.

According to a preferred embodiment the invention especially relates to the use of polymer beads or capsules as a host for endoparasitoids which beads or capsules are hydrophilic and porous, for instance biopolymer beads or capsules which are at least partly composed of alginate, carrageenan or chitosan, or mixtures thereof.

According to a more specific embodiment the invention relates to the use of biopolymer beads which are essentially composed of alginate wherein said alginate is a copolymer of beta-D-mannuronic acid and alpha-L-glucuronic acid, cross-linked by divalent cations, such as $Ca^{++}$ ions.

The term "at least partly" as used herein means from about 10% to almost 100%, for instance 20%, 30%, 40%, 50%, 60%, 70%, 80%, 90%, 95% or 99%.

The term "essentially" as herein used means that about 80 to 100% of its composition is alginate.

According to a preferred embodiment the invention relates to the use of polymer beads or capsules that are also essentially composed of Chitosan as a host for endoparasitoid wherein said chitosan is a derivative of chitin (poly-beta-(1-4)-2-amino-2-deoxy-D-glucopyranose) found in a large number of species of fungi, crustacea, insects and other Arthropods. As chitosan is the major component of insect cuticle, it is thus particularly well recognized by the endoparasitoid during oviposition and well suited for their development. The porous nature of the polymer matrix also allows the insect to perceive the inner composition of the media by antennal contact before oviposition.

The beads or capsules of the present invention can be used as a host for in vitro rearing of endoparasitoids, preferably hymenopterous endoparasitoids belonging to the order of insects (*Hymenoptera*).

Preferred endoparasitoids which are envisaged in the present invention to be reared using artificial hosts as described above, are chosen from the list of aphid endoparasitoids presented in Table 5.

Nevertheless, it should be clear that the present invention is not limited to rear aphid endoparasitoids but can also be used for other endoparasitoids.

It has been shown by the present inventors that additional stimuli can augment the success of oviposition by the endoparasitoids.

Therefore, the invention further relates to a method for in vitro rearing of endoparasitoids comprising the use of polymer beads or capsules as described or obtainable by any of the methods herein disclosed for oviposition wherein said endoparasitoids are placed in environment comprising wheat and/or their natural hosts. According to a further alternative the endoparasitoids are placed in an environment comprising wheat or parts of a plant, or plant odours and/or their natural hosts or the odours of these natural hosts.

Preferably when for instance hymenopterous endoparasitoids are to be reared when using polymer beads or capsules, the endoparasitoids are placed in an environment comprising wheat and cereal *aphids*. According to a further alternative the endoparasitoids are placed in an environment comprising wheat and cereal *aphids* or the odours of cereal *aphids*.

The beads or capsules themselves however may imitate the texture, the odor, the color and other characteristics or properties necessary for oviposition. As illustrated in the examples the colour of the bead or capsule may have a positive influence on oviposition. Therefore, according to a preferred embodiment, the polymer beads or capsules for use as a host for rearing endoparasitoids are yellow, preferably coloured yellow with STABILOBOSS™ yellow.

According to another embodiment, the invention also relates to the use of the polymer beads or capsules as described herein wherein said beads or capsules are coated with host epicuticular extract and/or plant extract.

The present invention further relates to any of the uses as described wherein said endoparasitoid is chosen from the group of hymenopterous endoparasitoids as listed in Table 5.

The invention further relates to a method for in vitro rearing (e.g. continuous) of an endoparasitoid comprising the steps of:
  the use of a biopolymer bead or capsule as herein described, said bead or capsule containing a nutritive solution, and
  bringing said bead or capsule in an oxygenated sterilized nutritive solution during endoparasitoid development.

Using the above method, the endoparasitoids may be continuously reared until the desired stage of development.

The invention thus relates to a method for rearing for in vitro rearing endoparasitoids until the stage of embed mummies comprising the step of collecting the bead or capsule when the endoparasitoid is an embedded mummy.

The invention also relates to a biopolymer bead or capsule comprising an embedded mummy of an endoparasitoid obtainable by the above described method.

To allow their survival and commercial distribution, it is important that these mummies are stored in a solution. The nutritive solution is a possibility but probably to expensive if it is only needed for distribution because during metamorphose parasitoids will not need nutrients. Water alone is not sufficient because of the osmotic pressure, the parasitoid mummies is hypertonic and so water will enter the bead and the mummy and will provoke damages to the endoparasitoids' cells by increasing the inner pressure. Therefore a more favourable way is to use a salt isotonic solution (for instance 0.007% NaCl buffered at a pH ranging from 6 to 7.5) or any other solution that has the same effect on the mummy and that can be used to preserve living tissues. So the final product may be the embedded mummy (mummies) in an isotonic salt solution. The farmer just needs to pulverize (e.g. disperse or spray) the solution. The release of a great quantity of parasitoids in a field, for instance a wheat field of several ha, in order that these parasitoids may be distributed evenly is a very difficult task. The present invention provides a concentrated amount of beads or capsules comprising the embedded mummies in a preservative solution which may be diluted according to the needs of the farmer or the machines he uses. The present invention thus allows just to spray (pulverize) the embedded mummies like an insecticide, using the classical systems (pulverisator; diffusers) every farmer or plant producer (horticulturist, gardener, etc.) has in his farm or company. The capsules or beads present in the solution will be dispersed evenly on the plants in the field and will dry just because the outdoor air is not saturated in water. When drying the biopolymer becomes sticky and will remain on the plant until the emergence of the parasitoid even if there is wind or rainfall. Under these conditions, on the plant the survival of the parasitoid before emergence will be better than just on the soil.

The term "pulverization" as used herein means spraying the solution containing the beads or capsules to allow their dispersion in the field, like an insecticide. A pneumatic system of pulverization or application may also be used to propel the beads or the capsules containing the mummies.

The invention also relates to a method for rearing for in vitro rearing endoparasitoids until the stage of adult emergence comprising the step of collecting the endoparasitoid when emerged from the bead or capsule.

The invention also relates to an endoparasitoid obtainable by (e.g. reared by) the methods described herein.

The invention further relates to the use of biopolymer bead or capsule or an endoparasitoid obtained by or obtainable by any of the methods of the invention for mass release in pest control.

According to another embodiment, the present invention relates to method for mass production of large amounts of endoparasitoids comprising pulverization of biopolymer beads or capsules obtainable by the methods herein described by placing said beads or capsules in an adequate solution and/or pulverization using a pulverisator Furthermore the invention provides a system for rearing endoparasitoids comprising:

- the use of at least one bead or capsule as defined above or obtainable by any of the methods of the invention,
- at least one endoparasitoid, and
- an environment suitable for oviposition of said endoparasitoid on said bead or capsule.

Said system may comprise at least one of the following:

- the use of host epicuticular extracts or pheromones and/or of plant extracts to coat the said bead or capsule to enhance oviposition of said endoparasitoid in said bead or capsule
- the use of host or plant odors for improving the attraction of the endoparasitoids towards the beads or capsules.
- a nutritive solution introduced inside the beads or capsules,
- a nutritive solution wherein said beads or capsules are immersed after oviposition, preferably the nutritive solutions inside and outside the beads or capsules are the same,
- a device allowing a continue flow of oxygenated and sterilized nutritive solution whereto beads or capsules are added during the endoparasitoid development, a device allowing the collect off the said beads or capsules at the end of the endoparasitoid development (pupal stage), possibly automated, a rear chamber at constant temperature in order to allow metamorphosis and adult emergence (e.g. end of larval stage, pupal stage and very young adults), a cold chamber (temperature ranging from −5° C. to +5° C.) with a humidity ranging between 70 and 100% allowing the storage of the embedded mummies (e.g. beginning of pupal stage) in function of the production necessity.

The term "embedded mummy" relates to the pupal stage (last developmental stage during which metamorphosis takes placed) of the endoparasitoid embedded inside the capsule or the bead in which it has spun a cocoon, before emergence of the adult. The pupae stage is very easy to visually recognize just by a glance, as just before pupation, the larval stage 3 endoparasitoids eject content of the digestive tract, what is call meconium. The meconium is very easy to see as it forms a small dark spot. As capsules and beads are nearly transparent, a dark spot is easy to identify just by a rapid check during production. For instance, when it is noted that most beads or capsules contain stage 3 larvae, the beads may be collected manually from the nutritive solution, or automatically, for instance by giving an apparatus an instruction (e.g., turning a knob or computer guided instructions) that the container comprising the beads or capsules and nutritive solution is emptied and beads or capsules are for instance filtered and transferred or transported to a following compartment or container where the next stage in development can proceed.

The rear chamber will receive the capsules or beads containing larval stage 3 at the end of its development to allow metamorphosis. Indeed at that moment for metamorphosis, full-developed Larva 3 do not eat anymore, and so do not need to be immersed in a nutritive solution. Metamorphosis is done using its fat and glycogen reserves. If the beads or capsules would remain in the nutritive solution at that stage of parasitoid development, the adult would be incapable to leave the capsules and will drown itself in the solution. In this respect, this step participates to the continuous rearing process.

The cold chamber is used to store the capsules or beads at the right temperature. Our experiments have shown that it is possible to store embedded mummies at about 3° C. under high humidity (e.g. from 70 to 100%), preferably under intermediate humidity (from 80 to 97%) at least for 3 to 5 weeks in quiescence stage, and possible longer for several months (1 to 6) in a diapause stage. It is likely to avoid saturated air to prevent the growth of fungi, which do not become visible in cold storage, but develop on the mummies when they are back at normal temperatures for development (e.g. 20° C.).

The term "quiescence" relates to the response of individual insects to a sudden unanticipated, non-cyclic and usually short deviation from normal weather conditions. As used herein, "quiescence" relates to a metabolic rest which can be induced by low temperature i.e. under the development threshold of the insect, currently about 6° C. but may depend on the parasitoid used. As soon as temperature increase over for instance 6° C. in the above case, the development goes on.

The term "diapause" relates to a hormonally-mediated state of low metabolic activity, associated with reduced morphogenesis, increased resistance to environmental extremes and altered or reduced behavioral activity. Diapause occurs during a genetically determined stage of development (e.g. at the pupal stage) in response to environmental cues (currently a reduction of the day duration like in autumn) that precedes unfavorable conditions (such as Winter). As used herein "diapause" relates to a metabolic rest that can be induced by low enlightenment duration mimicking weather conditions of autumn. At that stage the endoparasitoid remains alive during 3 to 6 month at low temperature.

The present system thus provides for several options, for instance the possibility of (1) only a rear chamber until the endoparasitoid emerges from the mummy, (e.g. collection of endoparasitoids), or (2) a rear chamber until the endoparasitoid is an embedded mummy and then transferred to a cold chamber for storage, (e.g. collection of beads with embed mummies). Other options provide for the collection of any other developmental stage of the endoparasitoid whenever there is a need thereof.

The system thus directly provides a means of producing parasitoids or beneficial insects at large scale. The said produced endoparasitoids or their embedded mummies, directly after production or storage, may be used for mass releases in the frame of biological control of insect pests. These releases may be done by hand or by any kind of dispersal devices. Embedded mummies may be placed in an adequate solution such as a salt physiological solution (NaCl, 0.07% buffered at a pH ranging from 6 to 7.5) and pulverized using a classical pulverisator. As when they dry, the said biopolymer constituting the bead or capsule become sticky, the embedded mummies will stick on the plant in good conditions before adult emergence. A pneumatic system of pulverization or application may also be used to propel the beads or the capsules containing the mummies. Both systems will allow a homogenous dispersal of the endoparasitoids where needed. They do not exclude the possible use of a slow release system like a diffuser system containing the said beads or capsules.

As used herein, the term "diffuser" relates to a device that allows to release slowly a certain amount of parasitoid per unit of time. It could be a box where the parasitoid or embedded mummies are stored with some food for the adult and that will allow the adults to meet inside after emergence and possibly to mate. It could be any other kind of device that will be placed in the fields, orchards or glasshouses allowing the emergence of adults and their release. It is an alternative to a spraying device or any kind of dispersal device.

The term "environment" in this aspect can relate to a physical entity as well as to physiological or environmental conditions wherein it would be possible that oviposition of the endoparasitoid to beads or capsules, serving as an artificial host for oviposition. A physical entity could be for instance a cage, a container, a green house comprising the beads or capsules and the endoparasitoid more or less closely together. Physiological or environmental conditions could for instance comprise the appropriate climate or climate regulation in term of temperature, light, humidity, etc, to establish optimal conditions for oviposition and optimal survival and rearing of eggs and larvae, other conditions such as the presence of wheat or cereal *aphids*, or other components providing odour or any other condition to mimic the natural environment of the endoparasitoid for oviposition.

According to another preferred embodiment said system comprises at one to several endoparasitoids chosen from the list of aphid endoparasitoids presented in Table 5.

The expression "at least one" as used herein relates to at least one in terms of numbers, such as "at least one organism or insect". Alternatively the expression "at least one" can also mean "at least one species", when for instance more than one kind of beneficial insect or endoparasitoid should be reared at the same time, and for each species one or more organism or insect can be contained within the system.

The invention, now being generally described, will be more readily understood by reference to the following tables, figures and examples, which are included merely for purposes of illustration of certain aspects and embodiments of the present invention and are not intended to limit the invention. All of the references mentioned herein are incorporated by reference.

The position of the needle is of importance as it needs be horizontal to produce good results.

Figure 1:
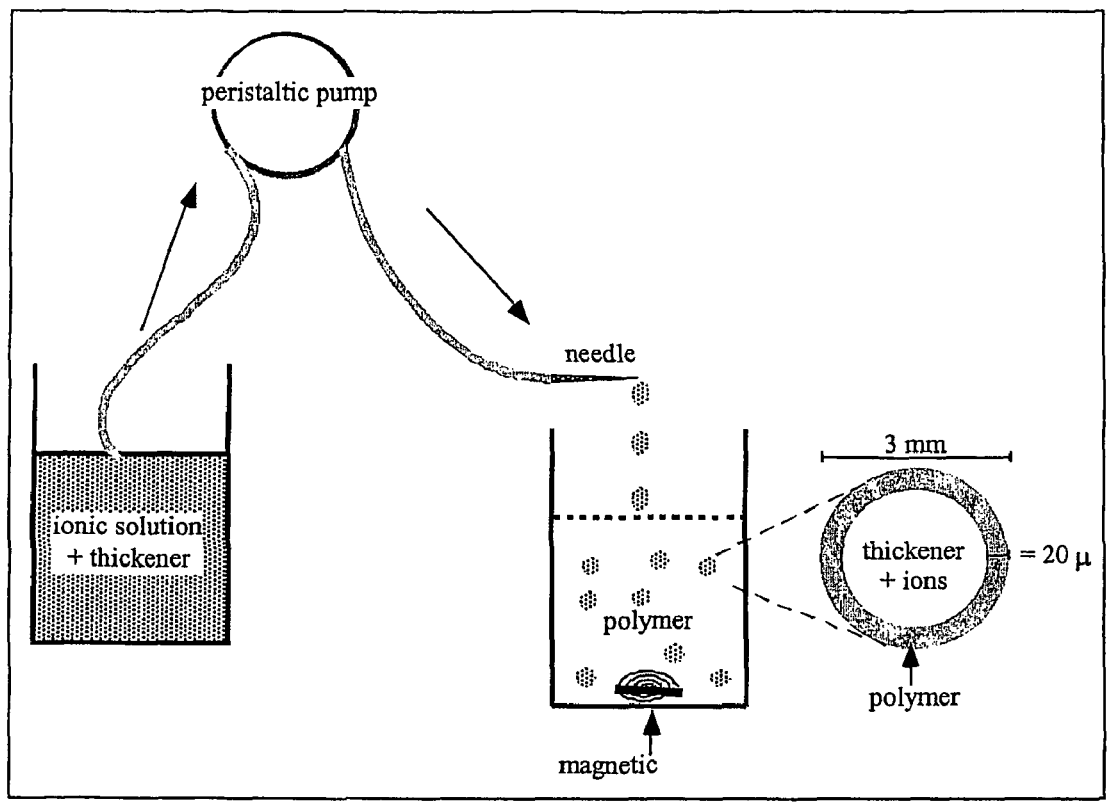
FIG. 1: Experimental design of the preparation of biopolymer capsules.
Figure 2:
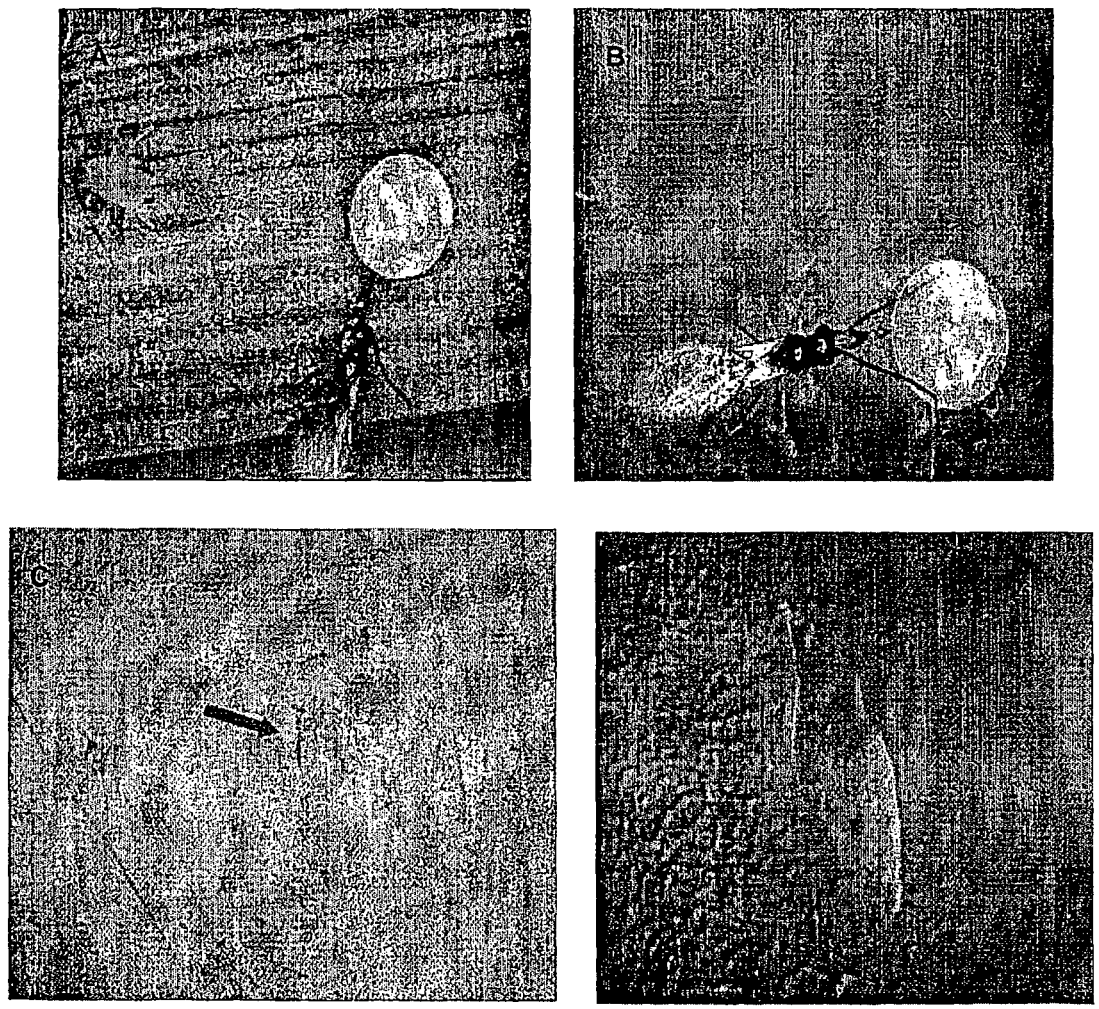

FIG. 2 A-D: Oviposition behavior of *Aphidius rhopalosiphi*.

Chitosan capsules are preferred to *aphids* (A). Presence of eggs in capsules after oviposition (C & D).

EXAMPLES

Example 1

Biopolymer Beads a) Description and Formation

1. Alginate Beads

Alginate occurs as the major structural polysaccharide of marine brown algae (*Phaeophyceae*). Chemically it is α (1→4)-linked linear block copolymer of β-D-mannuronic acid (M) and its C(5) epimer α-L-guluronic acid (G). The ratio M/G can strongly vary and is clearly correlate with the properties of alginates.

The formation of calcium alginate beads is the following. A solution containing 7,5 g/l of alginate (cecalgum: M/G=1,2) is dropped at room temperature through a needle to form droplets which fall into rapidly stirred 0,1 M solution of $CaCl_2$. A bead ($\phi$=2-3 mm) forms almost instantaneously due to the cross-linking of the alginate molecules by $Ca^{++}$ cations.

2. Chitosan Beads

Chitosan, poly-β-(1-4)-2-amino-2-deoxy-D-glucopyranose, is a derivative of chitin, a polysaccharide found in a wide variety of crustacea, insects, and fungi.

The formation of chitosan beads is the following. Chitosan 10 g/l is dissolved in a solution of acetic acid 14 ml/l. The solution is dropped at room temperature through a needle to form droplets which fall into rapidly stirred pentasodium tripolyphosphate (pH 8,6). Droplets instantly form a chitosan polyphosphate beads ($\phi$=2-3 mm). The beads are washed over to acetic acid and placed in pentasodium tripolyphosphate. After 30 minutes, beads are removed and rinsed with demineralized water b) Acceptance by the Endoparasitoid.

Chemical cues perceived by the endoparasitoid through receptors in the antennae and tarsi are undoubtedly of great importance in host acceptance. Size, shape, colour and surface texture of the host is also very important. If accepted at this stage, they attempt to probe the host with their ovipositor. Nevertheless, parasitoids frequently insert their ovipositor into a host but do not go on to lay an egg. The ovipositor is normally covered in sensillae and it seems likely that the insect is rejecting the host after perceiving that it is unsuitable for oviposition. The parasitoid may assess the suitability of the host using chemical cues. Thus, we tested polymer beads as host for the endoparasitoid *Aphidius rhopalosiphi*. We determined influence of the colour (Table 1), the polymer type, alginate and chitosan, (Table 2) and the environment (Table 3) the presence of trehalose inside the capsule Table 7 and plant or host extract (Table 6) on the behaviour of the parasitoid.

1. Effect of Colour on Oviposition Behaviour

Our results show that response, attack and acceptance of parasitoids are better on the beads coloured in yellow than on the not coloured beads. Furthermore, we observe that the beads coloured with STABILOBOSS™ yellow (Art.Nr. 070/24, Germany) frequently cause the attack and the acceptance of the parasitoid in comparison with beads coloured with E102 (Vahine BP17, 84170 Monteux, France). Consequently, alginate beads coloured in yellow with the STABILOBOSS™ yellow marker, are preferred examples of hydrogel beads.

2. Effect of Biopolymer (Alginate or Chitosan) on Oviposition Behaviour

Our results show that response, attack and acceptance of the parasitoid are better on alginate beads that on chitosan beads. This is probably caused by the difference of colour between the beads. Indeed, alginate and chitosan differently absorb the colorant (Stabilo®). However, concerning the capsules, the opposite results were found. Chitosan is more attractive than alginate.

3. Effect of Environment on Oviposition Behaviour

In order to determine effect of environment on oviposition behaviour of the endoparasitoid *Aphidius rhopalosiphi*, we placed alginate beads coloured with the Stabilo® in different environment:
  alone,
  with *aphids*,
  with wheat,
  with *aphids on wheat*.
Results are displayed in table 3.

The results show that the near environment of the parasitoid may influence its oviposition behaviour. Indeed, when beads are placed with *aphids* or wheat, response of the parasitoid is more frequent. Furthermore, the percentage of parasitoid acceptance (acceptance/response *100) is important (19%) when the beads are placed with *aphids* and is very important (32%) when the beads are placed in a patch (*aphids*+wheat) in comparison with the reference (4%). Thus, it is possible that odours released by *aphids* and wheat excite the parasitoids.

4. Effect of the Presence of Trehalose Inside Chitosan Capsules.

Four kind of nutritive solution inside yellow chitosan capsules were compared with regards to the oviposition behavior and the number of eggs laid inside the said capsules by the parasitoids *Aphidius rhopalosiphi*.
  Basic nutritive solution for parasitoids
  Aphids grinded solution
  Trehalose solution 0.6% introduced in the capsules by diffusion
  Trehalose solution incorporated in the ionic solution with dextran during the process of capsule formation It appeared that total number of attacked capsules, total number of capsules with eggs as well as the number of eggs collected in the capsules, and ratio between these two values are always higher in the case of Trehalose incorporated with dextran and secondly in trehalose incorporated by diffusion (Table 7). Yellow chitosan capsules containing trehalose are thus well suited for endoparasitoid oviposition. Eggs were found repeatedly in that kind of experiment.

5. Effect of Presence of Host Extracts on Oviposition Behaviour (See Table 7)

In order to determine the attractivity of epicuticular aphid compounds regarding endoparasitoids, epicuticular compounds were extracted from aphid exuviae using methanol. An exuviae is the cuticule remaining after the molting of the insect. This table shows the difference observed between oviposition behavior of *Aphidius rhopalosiphi* parasitoid on fresh exuviae (containing all epicuticular compounds), exuviae washed with methanol (Cold Meth) and exuviae re-applied with the methanol extract after washing. The behaviors measured are: of encounter (RENC), antennae contact (CA), abdomen fold (FOLD), ovipositor contact (CO), acceptance (FOLD+CO), and abdomen fold not follow by oviposition (FOLD Alone). It appeared that fresh exuviae as well as re-applied exuviae are more attractive than washed exuvia.

Further, an analysis is shown (Table 8) of the composition of the methanolic extract of epicuticular compounds belonging to the host that may be use to coat the beads or capsule in order to increase the level of oviposition in the beads or capsule. It was observed that this kind of extract with squalene increases the level of oviposition by the endoparasitoid in the bead or capsule.

Example 2

Biopolymer Capsules

Endoparasitoids often insert their ovipositor into the alginate beads coloured in yellow and placed in a "patch". Nevertheless, it does always go on to lay an egg. Thus, it is possible that the beads are not a good support of laying for the parasitoids. Consequently, other supports were tested. Three kinds of biopolymer capsules: chitosan/dextran, chitosan/lambda-carrageenan and alginate/dextran were tested in the following.

a) Description and Formation

1. Chitosan/Dextran

Chitosan/dextran capsules are produced as follows. A solution containing 1% chitosan dissolved in water containing 1,4% (v/v) acetic acid is kept stirred using a magnetic stirrer at room temperature. An aqueous suspension containing 1,5% sodium polyphosphate and 40% dextran is extruded through a needle generating small droplets ($\phi$=2-3 mm). Droplets instantly form a chitosan polyphosphate membrane enclosing the droplet. Capsules are removed from the solution and further treated in 1,5% sodium tripolyphosphate (pH 8,5) for half an hour. The capsules are rinsed and stocked in demineralized water.

2. Chitosan/Lambda-carrageenan

Chitosan/lambda-carrageenan capsules are produced as follows. A solution containing 1% chitosan dissolved in water containing 1,4% (v/v) acetic acid is kept stirred using a magnetic stirrer at room temperature. An aqueous suspension containing 1,5% sodium polyphosphate and 1,4% lambda-carrageenan is extruded through a needle generating small droplets ($\phi$=2-3 mm). Droplets instantly form a chitosan polyphosphate membrane enclosing the droplet. Capsules are removed from the solution and further treated in 1,5% sodium tripolyphosphate (pH 8,5) for half an hour. The capsules are removed and washed over to acetic acid 1,4%.

The capsules are placed in pentasodium tripolyphosphate. After 30 minutes, capsules are rinsed with demineralized water and stocked in demineralized water.

3. Alginate/Dextran

Alginate/dextran capsules are produced as follows. A solution containing 0,5% sodium alginate is prepared and kept stirred using a magnetic stirrer at room temperature. An aqueous suspension containing 1,3% $CaCl_2$ and 20% dextran is extruded through a needle generating small droplets ($\phi$=2-4 mm) which fall into rapidly stirred alginate solution. A capsular membrane forms almost instantaneously around the suspension drop to the cross-linking of the interfacial alginate molecules by $Ca^{++}$ cations. Prior to the removal of the capsules the polymer solution is diluted five-fold by adding required amount of milli-Q water. Finally, the capsules are removed and placed in a $CaCl_2$ 1,3% solution during 8 hours.

b) Acceptance by the Endoparasitoid.

Experiments showed that parasitoids laid eggs in the capsules of chitosan/dextran.

Example 3

Optimalisation of Preparation Methods for Biopolymer Capsules

In order to optimise the shape, diameter, porosity and wall thickness of the biopolymer beads, the protocol of Somesh et al. 1988 was dramatically changed at several points. An overview of these changes is given in Table 9. Important differences are noted in italic.

TABLE 1

Alginate biopolymer beads as host for the endoparasitoid *Aphidius rhopalosiphi*: influence of the bead colour.

|  | Without colour | E102 | STABILO ® |
| --- | --- | --- | --- |
| Response | 1.6 ± 2.6 | 16.6 ± 8.2 | 13.5 ± 7.2 |
| Attack | 0.3 ± 0.8 | 3.6 ± 3.1 | 6.5 ± 4.2 |
| Acceptance | 0 | 1.7 ± 2.0 | 4.3 ± 3.5 |

Response is defined as the number of meetings with the bead of 30 parasitoid females observed during 15 minutes.

Attack is defined as the number of bends of the abdomen underneath the thorax orienting the ovipositor tip toward the bead of 30 parasitoid females observed during 15 minutes.

Acceptance is defined as the number of contact with the ovipositor of 30 parasitoid females observed during 15 minutes.

E102 (1:1$H_2O$:E102) and Stabilo marker® (1:1$H_2O$ Stabilo) are used as yellow colorants.

TABLE 2

Beads as host for the endoparasitoid *Aphidius rhopalosiphi*: influence of the biopolymer.

|  | Response | Attack | Acceptance |
| --- | --- | --- | --- |
| Alginate | 13.5 ± 7.2 | 6.5 ± 4.2 | 4.3 ± 3.5 |
| Chitosan | 10.6 ± 5.7 | 3.1 ± 2.6 | 1.4 ± 1.7 |

Response is defined as the number of meetings with the bead of 30 parasitoid females observed during 15 minutes.

Attack is defined as the number of bends of the abdomen underneath the thorax orienting the ovipositor tip toward the bead of 30 parasitoid females observed during 15 minutes.

Acceptance is defined as the number of contact with the ovipositor of 30 parasitoid females observed during 15 minutes.

TABLE 3

Alginate biopolymer beads as host for the endoparasitoïd *Aphidius rhopalosiphi*: influence of the environment.

|  | Response | Attack | Acceptance |
|---|---|---|---|
| Alone | 12.4 ± 8.8 | 4.7 ± 5.0 | 0.5 ± 1.5 |
| Aphids | 20.1 ± 12.3 | 7.4 ± 7.7 | 3.9 ± 4.2 |
| Wheat | 25.2 ± 12.3 | 5.3 ± 5.3 | 1.3 ± 1.8 |
| Aphids + Wheat | 13.5 ± 7.2 | 6.5 ± 4.2 | 4.3 ± 3.5 |

Response is defined as the number of meetings with the bead of 30 parasitoid females observed during 15 minutes.

Attack is defined as the number of bends of the abdomen underneath the thorax orienting the ovipositor tip toward the bead of 30 parasitoid females observed during 15 minutes.

Acceptance is defined as the number of contact with the ovipositor of 30 parasitoid females observed during 15 minutes.

TABLE 4

Nutritive solution used to rear *Aphidius rhopalosiphi* larvae

| basal medium additives | SSM3[1] |
|---|---|
| trehalose | 600 mg/100 ml |
| vitamins | 1 ml (stock)[2] |
| FBS (fetal bovine serum) | 10% (v/v) |

[1]SSM3 composition

|  | Shields & Sang 1977 *drosophila* cell |
|---|---|
| Catalogue Number | S8398 |
| mg/100 ml |  |
| b-alanine | 25 |
| alanine | 150 |
| arginine | 50 |
| asparagine | 30 |
| aspartic acid | 30 |
| cysteine | 20 |
| cystine |  |
| glutamic acid | 1441 |
| glutamine | 60 |
| glycine | 50 |
| histidine | 55 |
| hydroxyproline |  |
| isoleucine | 25 |
| leucine | 40 |
| lysine | 85 |
| methionine | 25 |
| phenylalanine | 25 |
| proline | 40 |
| serine | 35 |
| threonine | 50 |
| tryptophan | 10 |
| tyrosine | 36 |
| valine | 40 |
| TOTAL amino acids | 2322 |

| Sugar | |
|---|---|
| glucose | 1000 |

| Vitamins | |
|---|---|
| Choline | 5 |

| Mineral salts | |
|---|---|
| Na2HPO4 | 88 |
| MgSO4 | 215 |
| CaCl2 | 76 |
| BIS-TRIS buffer | 105 |
| oxalacetic acid | 25 |

| divers | |
|---|---|
| yeast extract | 100 |
| pH | 6.4 |

[2]Vitamins composition (mg/100 ml)

| Biotin | 0.008 |
|---|---|
| Choline | 90 |
| Cyanocobalamine | 0.05 |
| folic acid | 0.06 |
| inositol | 5 |
| nicotinamide | 1 |
| pantothenic acid | 0.8 |
| pyridoxine | 0.01 |
| riboflavine | 0.008 |
| thiamine | 0.008 |

TABLE 5

Relations between plants, greenflies and parasitoids

| Greenfly | Host I | Host II | Parasitoïde |
|---|---|---|---|
| *Acyrtosiphon caraganae* |  |  | *Aphidius ervi* (Hal.) |
|  |  |  | *Toxares deltiger* (Hal.) |
| *Acyrtosiphon kindoi* |  |  | *Aphidius eadyi* |
|  |  |  | *Praon volucre* (Hal.) |
| *Acyrtosiphon pisum* (Harr.) |  | *Urtica dioica* L. | *Aphidius eadyi* |
|  |  | Family of legumes: *Vicia faba* L., pea, bean, clover | *Aphidius ervi* (Halyday) |
|  |  |  | *Aphidius picipes* |
|  |  |  | *Aphidius smithi* |
|  |  |  | *Aphidius urticae* |
|  |  |  | *Praon dorsale* |
|  |  |  | *Praon volucre* (Halyday) |
|  |  |  | *Toxares deltiger* (Hal.) |
| *Aphis fabae* (Scop.) | *Evonymus europaea* |  | *Aphidius colemani* (Vier.) |
|  |  |  | *Aphidius matriarcae* (Hal.) |
|  |  |  | *Ephedrus plagiator* (Nees) |
|  |  |  | *Lipolexis gracilis* (Förster) |
|  |  |  | *Lysiphlebus cardui* |
|  |  |  | *Lysiphlebus fabarum* (Marshall) |
|  |  |  | *Praon abjectum* (Hal.) |

TABLE 5-continued

Relations between plants, greenflies and parasitoids

| Greenfly | Host I | Host II | Parasitoïde |
|---|---|---|---|
| | | | *Praon volucre* (Hal.) |
| | | | *Trioxys angelicae* (Haliday) |
| *Brachycaudus helichrysi* | *Prunus spinosa* | Asteraceae | |
| *Brachycaudus* sp. | | | *Dysaphis* sp. |
| | | | *Ephedrus persicae* (Frog.) |
| | | | *Ephedrus plagiator* (Nees) |
| | | | *Lipolexis gracilis* (Förster) |
| | | | *Lysiphlebus fabarum* (Marshall) |
| | | | *Paralipsis enervis* (Nees) |
| | | | *Praon volucre* (Hal.) |
| | | | *Trioxys angelicae* (Halyday) |
| *Cinara* sp. | | | *Pauesia* sp. |
| *Diuraphis noxia* (Kurdjumov) | | | *Diaretiella rapae* (M'Intosh) |
| *Drepanisiphum platanoidis* | | *Acer* spp. | *Aphelinus thomsoni* (Graham) |
| *Elatobium abietinum* | | *Picea* | |
| *Forda* sp. | | | *Monoctonia pistaciaccola* |
| *Hyalopterus pruni* (Geoffr.) | *Prunus* | *Phragmites communis* | *Ephedrus plagiator* (Nees) |
| | | | *Praon volucre* (Halyday) |
| *Macrosiphon pisum* | | Family of legumes | *Aphidius ervi* (Hal.) |
| *Macrosiphum euphorbiae* | *Rosa* spp. | Solanaceae | *Aphidius ervi* (Hal.) |
| | | | *Aphidius nigripes* |
| *Metopolophium dirhodum* | *Rosa* spp. | Grasses | *Aphelinus abdominalis* |
| | | | *Aphidius ervi* (Hal.) |
| | | | *Aphidius picipes* |
| | | | *Aphidius rhopalosiphi* |
| | | | *Aphidius ukbekistanicus* |
| | | | *Ephedrus plagiator* (Nees) |
| | | | *Praon volucre* (Hal.) |
| | | | *Toxares deltiger* (Hal.) |
| *Metopolophium fetuscae* (Theobald) | | | *Aphidius ervi* (Hal) |
| | | | *Aphidius picipes* |
| | | | *Aphidius rhopalosiphi* |
| | | | *Aphidius uzbekistanicus* |
| *Microlophium carnosum* (Buckton) | | *Urtica dioica* | *Aphidius ervi* (Hal.) |
| | | | *Aphidius picipes* (Nees) |
| | | | *Aphidius urticae* |
| *Microlophium evansi* | | *Urtica dioica* L. | *Aphidius ervi* (Hal.) |
| *Mindarus abietinus* (Koch) | | | *Pseudopraon minderphagum* |
| *Myzus persicae* | *Prunus persicae* | Potato | *Aphidius colemani* |
| | | Turnip | *Aphidius ervi* (Hal.) |
| | | Chrysanthenum | *Aphidius matricariae* |
| | | Brassicacae (cultivars) | *Diaretiella rapae* (M'Intosh) |
| | | | *Ephedrus cerasicola* |
| | | | *Ephedrus plagiator* (Nees) |
| *Ononis* spp. | | *Urtica dioica* L. | |
| *Pemphigus* sp. | | | *Monoctonia pistaciaecola* |
| *Periphyllus acericola* (Walker) | | *Acer pseudoplatanus* | *Praon sylvestre* (Stary) |
| | | | *Trioxys flacatis* (Alaekauer) |
| *Periphyllus aceris* (Linnaeus) | | *Acer platanoides* | *Praon sylvestre* (Stary) |
| | | | *Trioxys flacatis* (Alaekauer) |
| *Periphyllus coracinus* (Koch) | | *Acer platanoides* | *Aphidius setiger* |
| | | | *Trioxys glacatus* (Alaekauer) |
| *Periphyllus hirticornis* (Walker) | | *Acer campestre* | *Aphidius setiger* |
| | | | *Praon sylvestre* (Stary) |
| | | | *Trioxys flacatus* (Alaekauer) |
| *Periphyllus lyropictres* (Kessler) | | *Acer platanoides* | *Aphidius setiger* |
| | | *Acer pseudoplatanus* | *Trioxys flacatis* (Alaekauer) |
| *Periphyllus obscurus* (Mamontova) | | *Acer campestre* | *Trioxys flacatus* (Alaekauer) |
| *Periphyllus* sp. | *Acer* spp. | | *Praon sylvestre* |
| *Periphyllus testudinaceus* (Fernie) | | *Acer campestre* | *Praon sylvestre* (Stary) |
| | | *Acer platanoides* | *Trioxys flacatis* (Alaekauer) |
| | | *Acer pseudoplatanus* | |
| *Protolachnus* sp. | | | *Diaretus leucopterus* (Hal.) |
| *Rhopalosiphum padi* | *Prunus padus* L. | Crops | *Diaretiella rapae* (M'Intosh) |
| | | *Capsella bursa-pastoris* | *Trioxys angelicae* (Halyday) |
| *Schizolachnus* sp. | | | *Pauesia unlilachni* (Gahan) |
| *Schizophis graminum* (Rondoni) | | Sorgho | *Aphidius rhopalosiphi* |
| | | Orge | *Lysiphlebus testaceipes* (Cresson) |
| *Sitobion avenae* | | Grasses | *Aphidius avenaphis* (Fitch) |
| | | | *Aphidius ervi* (Hal.) |
| | | | *Aphidius picipes* (Nees) |
| | | | *Aphidius rhopalosiphi* |
| | | | *Aphidius uzbekistanicus* |

TABLE 5-continued

Relations between plants, greenflies and parasitoids

| Greenfly | Host I | Host II | Parasitoïde |
|---|---|---|---|
| Sitobion fragariae | Rubus fructicosus | Grasses: Avena sativa L. Digitalis sp. | Diaretiella rapae (M'Intosh)<br>Ephedrus plagiator (Nees)<br>Praon volucre (Hal.)<br>Toxares deltiger (Hal.)<br>Aphidius ervi (Hal.)<br>Aphidius rhopalosiphi |

TABLE 6

Consequence of Trehalose presence on the oviposition behaviuor of Aphidius rhopalosiphi.

| Parametres | T | $Th_{Dex}$ | $Th_{Diff}$ | JP |
|---|---|---|---|---|
| Total nb of capsules | 60 | 60 | 60 | 60 |
| % attacked capsules | 23.33% | 46.67% | 46.67% | 36.67% |
| Nb of attacks per attacked capsules | 2.57 | 5.04 | 11.43 | 4.86 |
| Nb of capsules with eggs | 0 | 6 | 1 | 0 |
| % of capsules with eggs/total capsules | — | 10% | 1.67% | — |
| % of capsules with eggs/total attacked capsules | — | 21.42% | 3.57% | — |
| Total number of eggs found inside the capsules | 0 | 10 | 2 | 0 |
| % eggs/total capsules | — | 16.67% | 3.33% | — |
| % eggs/total attacked capsules | — | 35.71% | 7.14% | — |

T: Control capsule: Chitosan capsule + yellow stabilo
$Th_{Dex}$: yellow capsules + trehalose mixed with dextran.
$Th_{Diff}$: yellow capsules + trehalose introduced by diffusion.
JP: yellow capsules containing extracts of grinded aphids.

TABLE 7

Attractivity of epicuticular aphid compounds regarding endoparasitoids

| Behavior | Fresh | REAPP | Cold METH |
|---|---|---|---|
| RENC | 31.0 | 40.2 | 15.2 |
| CA | 21.7 | 16.6 | 5.5 |
| FOLD | 3.7 | 2.2 | 0.8 |
| CO | 8.5 | 2.7 | 1.7 |
| ACCEPT | 12.1 | 4.9 | 2.5 |
| FOLD Alone | 3.7 | 2.2 | 0.8 |

TABLE 8

Composition of the methanolic extract. Squalene was also present.

| Identified molecules | retention time (min) |
|---|---|
| methyle tetradecanoate | 9.98 |
| methyl 9-methyl tetradecanoate | 11.32 |
| methyl cis-9-octadecanoate | 12.45 |
| methyl hexadecanoate | 12.73 |
| methyl cis,cis-9-12-octadienoate | Near the following peak |
| methyl cis-9-octadecenoate | 15.28 |
| methyl octadecanoate | 15.59 |

TABLE 9

Modification to protocol for preparation of chitosin capsules for oviposition.

| | Somesh et al. 1988: Techniques for preparing hydrogel membrane capsules | Invention |
|---|---|---|
| Polymer Solution | 1% (w/v) of Chitosan (Sigma) 1.4% (v/v) acetique acid. | 0.75% (w/v) of Chitosan <<medium>> 1.4% (v/v) acetique acid |
| Ionic Solution | 1.5% (w/v) pentasodium-tri-polyphosphate 40% (w/v) Dextran (Sigma). | 2.5% (w/v) pentasodium tri-polyphosphate 20% (w/v) Dextran (Sigma) |
| Duration in chitosan | No data | 5 min (essential to control the thickness of the walls) |
| Rinsing of capsules | acetique acid 1.4% (v/v) | acetique acid 1.4% (v/v) |
| Maturation time | 30 min in pentasodium-tri-polyphosphate 1.5% | 15 min in pentasodium tri-polyphosphate 2.5% (w/v) |
| Agitation of polymer solution | No data | 600 rpm |
| Diameter of the needle | Not given | 0.45 mm |
| Delivery rate of ionic solution | Not given | 7 ml/min (ou 100 droppletss/min) |
| pH | Not given | pH of polymer solution: 3.5 (obligatory t < 5.5) pH of ionic solution: range between 6 to 9 |

TABLE 9-continued

Modification to protocol for preparation of chitosin capsules for oviposition.

| | Somesh et al. 1988: Techniques for preparing hydrogel membrane capsules | Invention |
|---|---|---|
| | Characteristics favouring the oviposition in the capsules | |
| Capsules color | No object | Stabilobloss at 4% |
| Capsules content | No object | Trehalose |

REFERENCES

Grenier et al. (1994) in Pest Management in the Subtropics, Biological Control-a Florida Perspective, Eds, D., Rosen, F. D. Bennett, and J. L. Capinera, Intercept Press, Andover, U. K., Chapter 10, pp. 181-205.

Hoffman, J. D., Ignoffo, C. M. (1974). Growth of *Pteromalus puparum* in a semi-synthetic medium. Ann. Ent. Soc. Am. 67, 524-525.

Hoffman, J. D., Ignoffo, C. M and Dickerson, W. A. (1975). In vitro rearing of the endoparasitic wasp, *Trichogramma pretiosum*. Ann. Ent. Soc. Am. 68, 335-336.

House, H. L. (1978) An artificial host: Encapsulated synthetic medium for in vitro oviposition and rearing the endoparasitoid *Itoplectis conquisitor* (*Hymenoptera: Ichneumonidae*). Canadian entomologist. 110, 331-333.

Pennacchio, F., Vinson, S. B., Tremblay, E. (1992). Preliminary results on in vitro rearing of the endoparasitoid *Cardichiles nigriceps* from egg to second instar. Entomol. Exp. Appl., 64, 209-216.

Simmonds, F. J. (1966). Insect parasites and predators. In Insect Colonization and Mass production (Ed. By Smith C. N.), pp. 489-499. Academic Press, New York.

Somesh C. Nigam, I-Fu Tsao, Akiyoshi Sokada and Henry Y. Wang 1988. Techniques for preparing hydrogel membrane capsules. Biotechnology Techniques Vol 2 n°4. pp 271-276 Annexe 1

Velings N. (1997): Propriétés physico-chimiques des billes d'alginates et leur influence sur l'incorporation ou le relargage de molécules bioacives. Université catholique de Louvain (UCL).

Wang Henry Y; Nigam Somesh (1995) U.S. Pat. No. 5,427,935 Hybrid membrane bead for encapsulating materials in semi-permeable hybrid membranes.

Yagzan, S. (1972). A chemically defined synthetic diet and larval nutritional requirements of the endoparasitoid *Itoplectis conquisitor*. Journal of insect physiology, 18, 2123-2141.

What is claimed is:

1. A method of rearing an endoparasitoid comprising: rearing the endoparasitoid in a spherical biopolymer bead or capsule, whereby the bead or capsule acts as a host for the endoparasitoid.

2. The method according to claim 1 for in vitro rearing of endoparasitoids.

3. The method according to claim 1 wherein said biopolymer bead or capsule is used for oviposition and continuous rearing of an endoparasitoid from the egg through to the adult emergence of said endoparasitoid.

4. The method according to claim 1 wherein said biopolymer bead or capsule is hydrophilic and porous.

5. The method according to claim 1 wherein said biopolymer bead or capsule is composed of alginate, carrageenan or chitosan, or mixtures thereof 6. The method according to claim 5 wherein said biopolymer bead or capsule is essentially composed of alginate, wherein said alginate is a copolymer of beta-D-mannuronic acid and alpha-L-glucuronic acid, crosslinked by divalent cations.

7. The method according to claim 5 wherein said biopolymer bead or capsule is essentially composed of chitosan, wherein said chitosan is a derivative of chitin (poly-beta-(1-4)-2-amino-2-deoxy-D-glucopyrano.)

8. The method according to claim 1 wherein said polymer bead or capsule is essentially yellow.

9. The method according to claim 8 wherein said polymer bead or capsule is colored yellow with STABILOBOSS™ yellow.

10. The method according to claim 1 wherein said biopolymer bead or capsule is coated with host epicuticular extract and/or plant extract.

11. The method according to claim 1 wherein said endoparasitoid is selected from the group consisting of hymenopterous endoparasitoids selected from *Aphidius ervi* (Hal.), *Toxares deltiger* (Hal.), *Aphidius eadyi, Praon volucre* (Hal.), *Aphidius picipes, Aphidius smithi, Aphidius urticae, Praon dorsale, Aphidius colemani* (Vier.), *Ephedrus plagiator* (Nees), *Lipolexis gracilis* (Förster), *Lysiphlebus cardui, Lysiphlebus fabarum* (Marshall), *Praon abjectum* (Hal.), *Trioxys angelicae* (Haliday), *Dysaphis sp., Ephedrus persicae* (Frog.), *Paralipsis enervis* (Nees), *Pauesia*sp., *Diaretiella rapae* (M'Intosh), *Aphelinus thomsoni* (Graham), *Aphidius nigripes, Aphelinus abdominalis, Aphidius uzbekistanicus, Pseudopraon minderphagum, Aphidius matricariae, Ephedrus cerasicola, Monoctonia pistaciaecola, Praon sylvestre* (Stary), *Aphidius setiger, Trioxys glacatus* (Alaekauer), *Trioxys flacatus* (Alaekauer), *Diaretus leucopterus* (Hal.), *Pauesia unlilachni* (Gahan), *Lysiphlebus testaceipes* (Cresson), *Aphidius avenaphis* (Fitch), *Aphidius uzbekistanicus,* or *Aphidius rhopalosiphi.*

12. The method for rearing an endoparasitoid according to claim 1 further comprising placing said endoparasitoid in an environment comprising wheat and/or a natural host of the endoparasitoid and/or an odor of the natural host.

13. The method for rearing of an endoparasitoid according to claim 1 further comprising placing said endoparasitoid in an environment comprising wheat and/or cereal *aphids.*

14. A system for rearing endoparasitoids comprising:
at least one bead or capsule as defined in claim 1,
at least one endoparasitoid, and
an environment suitable for oviposition of said endoparasitoid on said bead or capsule.

15. A method for continuous in vitro rearing of an endoparasitoid comprising the steps of:

laying an egg of an endoparasitoid in a spherical biopolymer bead or capsule which comprises a nutritive solution, and maintaining said bead or capsule in an oxygenated sterilized nutritive solution during endoparasitoid development.

16. A method according to claim 15 further comprising the steps of: in vitro rearing said endoparasitoid in said bead or capsule until the stage of embed mummies and collecting the bead or capsule when the endoparasitoid is an embed mummy.

17. A biopolymer bead or capsule comprising an embed mummy of an endoparasitoid obtainable by the method of claim 16.

18. A method of treating a pest which comprises administering the biopolymer bead or capsule of claim 17 to a pest population.

19. A method for mass production of large amounts of endoparasitoids comprising pulverization of biopolymer beads or capsules obtainable by the method of claim 16 by placing said beads or capsules in an adequate solution and/or pulverization using a pulverisator.

20. A method according to claim 15 further comprising the steps of: in vitro rearing said endoparasitoid in said bead or capsule until the stage of adult emergence mummies and collecting the endoparasitoid emerged from the bead or capsule.

* * * * *

UNITED STATES PATENT AND TRADEMARK OFFICE
CERTIFICATE OF CORRECTION

PATENT NO. : 7,789,039 B2
APPLICATION NO. : 10/481102
DATED : September 7, 2010
INVENTOR(S) : Hance et al.

It is certified that error appears in the above-identified patent and that said Letters Patent is hereby corrected as shown below:

Column 2, Line 52, "without loosing" should be changed to --without losing--

Column 4, Lines 57-58, "trippolyphospate and" should be changed to --tripolyphosphate and--

Column 5, Lines 48-49, "of the capsule," should be changed to --of the capsule.--

Column 7, Line 15, "tripolyphospahte (ionic" should be changed to --tripolyphosphate (ionic--

Column 7, Lines 34-35, "octadecyle hexadodecanoate" should be changed to --octadecyl hexadodecanoate--

Column 7, Line 37, "B-farnesne and/or" should be changed to --B-farnesene and/or--

Column 7, Lines 66-67, "said endoparasitoid" should be changed to --said endoparasitoid.--

Column 9, Line 60, "probably to expensive" should be changed to --probably too expensive--

Column 10, Line 45, "using a pulverisator" should be changed to --using a pulverisator. --

Column 13, Lines 50-51, "demineralized water" should be changed to --demineralized water.--

Column 17, TABLE 3, Line 1, "for the endoparasitold" should be changed to --for the endoparasitoid--

Column 18, TABLE 4, Line 28, "oxalacetic acid" should be changed to --oxaloacetic acid--

Columns 17-18, TABLE 5, Line 15, "*Evonymus europaea*" should be changed to --*Euonymus europaea*--

Column 21, TABLE 6, Line 2, "behaviuor of" should be changed to --behavior of--

Column 22, TABLE 8, Line 3, "methyle tetradecanoate" should be changed to --methyl tetradecanoate --

Column 22, TABLE 9, Line 1, "of chitosin capsules" should be changed to --of chitosan capsules--

Column 22, TABLE 9, Line 19, "droppletss/min" should be changed to --droplets/min--

Column 23, TABLE 9, Line 1, "of chitosin capsules" should be changed to --of chitosan capsules--

Column 23, Line 41, "Annexe 1" should be changed to --Annexe 1.--

Signed and Sealed this
First Day of March, 2011

David J. Kappos
*Director of the United States Patent and Trademark Office*

CERTIFICATE OF CORRECTION (continued)
U.S. Pat. No. 7,789,039 B2

Column 23, Line 44, "molécules bioacives." should be changed to --molécules bioactives.--

Column 24, Line 16, "mixtures thereof" should be changed to --mixtures thereof.--

Column 24, Line 25, "D-glucopyrano." should be changed to --D-glucopyranose.--

Column 24, Line 43, "*Pauesia*sp., *Diaretiella*" should be changed to --*Pauesia* sp., *Diaretiella*--